US011053508B2

(12) United States Patent
Bawdon et al.

(10) Patent No.: US 11,053,508 B2
(45) Date of Patent: Jul. 6, 2021

(54) ENHANCED PROCESSES AND REAGENTS FOR HOST ENGINEERING

(71) Applicant: INV Nylon Chemicals Americans, LLC, Wilmington, DE (US)

(72) Inventors: Daniel Bawdon, County Durham (GB); Stephen Thomas Cartman, Eaglescliffe (GB); Jonathan Kennedy, North Yorkshire (GB)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 445 days.

(21) Appl. No.: 15/717,216

(22) Filed: Sep. 27, 2017

(65) Prior Publication Data
US 2018/0100160 A1   Apr. 12, 2018

Related U.S. Application Data

(60) Provisional application No. 62/402,302, filed on Sep. 30, 2016.

(51) Int. Cl.
| | |
|---|---|
| *C12N 15/74* | (2006.01) |
| *C12N 15/64* | (2006.01) |
| *C12N 13/00* | (2006.01) |
| *C12N 9/22* | (2006.01) |
| *C12N 15/52* | (2006.01) |

(52) U.S. Cl.
CPC .............. *C12N 15/74* (2013.01); *C12N 9/22* (2013.01); *C12N 13/00* (2013.01); *C12N 15/52* (2013.01); *C12N 15/64* (2013.01); *C12Y 301/21* (2013.01)

(58) Field of Classification Search
None
See application file for complete search history.

(56) References Cited

U.S. PATENT DOCUMENTS

| | | | |
|---|---|---|---|
| 6,706,525 B1 * | 3/2004 | Greener | C12N 15/70 435/252.1 |
| 2005/0032225 A1 * | 2/2005 | Blattner | C12N 1/08 435/488 |
| 2010/0055739 A1 * | 3/2010 | Thomas | C12N 9/1007 435/69.1 |
| 2018/0327757 A1 * | 11/2018 | Bongiorni | C12N 9/1247 |

FOREIGN PATENT DOCUMENTS

| | | |
|---|---|---|
| JP | 2013005792 | 1/2013 |
| WO | 2013173711 | 11/2013 |

OTHER PUBLICATIONS

International Search Report and Written Opinion in PCT/US2017/053611 dated Feb. 2, 2018.
International Preliminary Report on Patentability in PCT/US2017/053611 dated Apr. 2, 2019.
Croux et al. "Construction of a restriction-less marker-less mutant useful for functional genomic and metabolic engineering of the biofuel producer Clostridium acetobutylicum" Biotechnology Biofuels 2016 9:1-13.
Ewering et al. "Metabolic engineering of strains of Ralstonia eutropha and Pseudomonas putida for biotechnological production of 2-methylcitric acid" Metabolic Engineering 2006 8 587-602.
Grousseau et al. "Isopropanol production with engineered Cupriavidus necator as bioproduction platform" Appl Microbiol Biotechnol 2014 98:4277-4290.
Hobson et al. "Generation of a restriction minus enteropathogenic *Escherichia coli* E2348/69 strain that is efficiently transformed with large, low copy plasmids" BMC Microbiology 2008 8(134):1-10.
Pohlmann et al. "Genome sequence of the bioplastic-producing "Knallgas" bacterium *Ralstonia eutropha* H16" Nature Biotechnology 2006 1-6.
Bertram et al., "The Application of Tet Repressor in Prokaryotic Gene Regulation and Expression", Microbial Biotechnology, vol. 1, issue 1, Jan. 2008, pp. 2-16.
Gibson et al., "Enzymatic Assembly of DNA Molecules Up to Several Hundred Kilobases", Nature Methods, vol. 6, No. 5, May 2009, pp. 343-345.
Jouhten et al., "Yeast Metabolic Chassis Designs for Diverse Biotechnological Products", Scientific Reports, Altmetric 6, Citations 2, Article No. 29694, 2016, pp. 1-9.
Kovach et al., "Four New Derivatives of the Broad-Host-Range Cloning Vector pBBR1MCS, Carrying Different Antibiotic-Resistance Cassettes", Gene, vol. 166, Issue 1, Dec. 1, 1995, pp. 175-176.
Stavropoulos et al., "Expression of the tetA(C) Tetracycline Efflux Pump in *Escherichia coli* Confers Osmotic Sensitivity", FEMS Microbiology Letters, vol. 190, Issue 1, Sep. 1, 2000, pp. 147-150.
Unthan et al., "Chassis Organism from Corynebacterium Glutamicum—a Top-Down Approach to Identify and Delete Irrelevant Gene Clusters", Biotechnology Journal, vol. 10, Issue 2, Feb. 2015, pp. 290-301.
Waters et al., "The Tetracycline Resistance Determinants of RP1 and Tnl721: Nucleotide Sequence Analysis", Nucleic Acids Research, vol. 11, Issue 17, Sep. 10, 1983, pp. 6089-6105.

(Continued)

*Primary Examiner* — Antonio Galisteo Gonzalez

(57) ABSTRACT

Nonnaturally occurring host cells altered to increase their ability to transfer genetic molecules into the host cells as compared to an unaltered host cell are provided. Also provided are methods for identifying endogenous loci of a host cell which inhibit transformation efficiency and/or electroporation of genetic molecules into the cell as well as methods for producing nonnaturally occurring host cells with enhanced transformation efficiency and/or the modified ability to allow for genomic integration of an exogenous DNA sequence via electroporation. Methods for producing biochemicals and products produced with the nonnaturally occurring host cells are also provided.

5 Claims, 2 Drawing Sheets
Specification includes a Sequence Listing.

(56) References Cited

OTHER PUBLICATIONS

Woodruff et al., "Towards a Metabolic Engineering Strain Commons: An *Escherichia coli* Platform Strain for Ethanol Production", Biotechnology and Bioengineering, vol. 110, Issue 5, May 2013, pp. 1520-1526.

* cited by examiner

DNA from H16　　　　DNA from *E. coli*

(100 ng plasmid DNA electroporated)

SEQUENCE LISTING

```
<160> NUMBER OF SEQ ID NOS: 1

<210> SEQ ID NO 1
<211> LENGTH: 2121
<212> TYPE: DNA
<213> ORGANISM: Artificial sequence
<220> FEATURE:
<223> OTHER INFORMATION: Synthetic

<400> SEQUENCE: 1
tcagcgatcg gctcgttgcc ctgcgccgct ccaaagcccg cgacgcagcg ccggcaggca      60
gagcaagtag agggcagcgc ctgcaatcca tgcccacccg ttccacgttg ttatagaagc     120
cgcatagatc gccgtgaaga ggaggggtcc gacgatcgag gtcaggctgg tgagcgccgc     180
cagtgagcct tgcagctgcc cctgacgttc ctcatccacc tgcctggaca acattgcttg     240
cagcgccggc attccgatgc cacccgaagc aagcaggacc atgatcggga acgccatcca     300
tccccgtgtc gcgaaggcaa gcaggatgta gcctgtgccg tcggcaatca ttccgagcat     360
gagtgcccgc ctttcgccga gccgggcggc tacagggccg gtgatcattg cctgggcgag     420
tgaatgcaga atgccaaatg cggcaagcga aatgccgatc gtggtcgcgt cccagtgaaa     480
gcgatcctcg ccgaaaatga cccaaagcgc ggccggcacc tgtccgacaa gttgcatgat     540
gaagaacacc gccatcaggg cggcgacgac ggtcatgccc cgggcccacc ggaacgaagc     600
gagcgggttg agagcctccc ggcgtaacgg ccggcgttcg cctttgtgcg actccggcaa     660
aaggaaacag cccgtcagga aattgaggcc gttcaaggct gccgcggcga agaacggagc     720 gtgggggag aaaccgccca tcagcccacc gagcacaggt cccgcgacca tcccgaaccc     780
gaaacaggcg ctcatgaagc cgaagtgccg cgcgcgctca tcgccatcag tgatatcggc     840
aatataagcg ccggctaccg ccccagtcgc cccggtgatg ccggccacga tccgcccgat     900
atagagaacc caaaggaaag gcgctgtcgc catgatggcg tagtcgacag tggcgccggc     960
cagcgatacg agcaagattg gccgccgccc gaaacgatcc gacagcgcgc ccagcacagg    1020
tgcgcaggca aattgcacca acgcatacag cgccagcaga atgccatagt gggcggtgac    1080
gtcgttcgag tgaaccagat cgcgcaggag gcccggcagc accggcataa tcaggccgat    1140
gccgacagcg tcgagcgcga cagtgctcag aattacgatc aggggtatgt tgggtttcac    1200
```

-continued

```
gtctggcctc cggaccagcc tccgctggtc cgattgaacg cgcggattct ttatcactga    1260
taagttggtg gacatattat gtttatcagt gataaagtgt caagcatgac aaagttgcag    1320
ccgaatacag tgatccgtgc cgccctggac ctgttgaacg aggtcggcgt agacggtctg    1380
acgacacgca aactggcgga acggttgggg gttcagcagc cggcgcttta ctggcacttc    1440
aggaacaagc gggcgctgct cgacgcactg gccgaagcca tgctggcgga gaatcatacg    1500
cattcggtgc cgagagccga cgacgactgg cgctcatttc tgatcgggaa tgcccgcagc    1560
ttcaggcagg cgctgctcgc ctaccgcgat ggcgcgcgca tccatgccgg cacgcgaccg    1620
ggcgcaccgc agatggaaac ggccgacgcg cagcttcgct tcctctgcga ggcgggtttt    1680
tcggccgggg acgccgtcaa tgcgctgatg acaatcagct acttcactgt tggggccgtg    1740
cttgaggagc aggccggcga cagcgatgcc ggcgagcgcg gcggcaccgt tgaacaggct    1800
ccgctctcgc cgctgttgcg ggccgcgata gacgccttcg acgaagccgg tccggacgca    1860
gcgttcgagc agggactcgc ggtgattgtc gatggattgg cgaaaaggag gctcgttgtc    1920
aggaacgttg aaggaccgag aaagggtgac gattgatcag gaccgctgcc ggagcgcaac    1980
ccactcacta cagcagagcc atgtagacaa catcccctcc cccttccac cgcgtcagac    2040 gcccgtagca gcccgctacg ggcttttttca tgccctgccc tagcgtccaa gcctcacggc    2100
cgcgctcggc ctctctggcg c                                              2121
```

ENHANCED PROCESSES AND REAGENTS FOR HOST ENGINEERING

This patent application claims the benefit of priority from U.S. Provisional Application Ser. No. 62/402,302, filed Sep. 30, 2016, teachings of which are incorporated herein by reference in their entirety.

FIELD

The present invention relates to nonnaturally occurring hosts altered to increase their ability to transfer genetic molecules into the host and methods for their production and use in producing biochemicals and products comprising the biochemicals. The present invention also relates to methods for identifying endogenous loci of a host which inhibit transformation efficiency and/or electroporation of genetic molecules into the cell.

BACKGROUND

The number and diversity of industrially important molecules for which microbial production routes have been demonstrated is increasing. The range of chemicals that can be produced microbially has expanded substantially, in part due to advances in the field inclusive of: DNA sequencing efforts that have revealed new metabolic reactions and variants of enzymes from many different organisms; databases of gene expression, metabolic reactions, and enzyme structures allowing for query of desired reactions and design; genetic tools providing for more precise control over metabolic pathways; and analytical tools which allow for tracking of RNA, proteins, and metabolites in a cell; and detailed models of biology which aid in the design of enzymes and metabolic pathways. However, microbes are not always as malleable as organic chemistry. Genes may not be expressed, and the resulting enzymes may not function in every host; products or metabolic intermediates may be toxic to one host but not another host; different hosts have different levels of sophistication of genetic tools available; and processing conditions (e.g., growth, production, product separation and purification) are not compatible with all hosts.

In this era of genome-engineering, it is increasingly important that researchers have access to a common set of platform strains that can serve as production chassis and the basis for applying new metabolic engineering strategies for modeling and characterizing flux, engineering complex traits, and optimizing overall performance. Platform strains of *E. coli* (Woodruff et al. Biotechnol Bioeng. 2013 May; 110(5):1520-6. doi: 10.1002/bit.24840. Epub 2013 Jan. 29; http:// with the extension parts.igem.org/*Escherichia_coli*_chassis) *Corynebacterium glutamicum* ATCC 13032 (Unthan et al. Biotechnol. J. 2015 10:290-301) and *Saccharomyces cerevisiae* (Jouhten et al. Scientific Reports 2016 6:29694 DOI:10.1038/srep29694) have been described.

Hosts with increased ability to transfer genetic molecules are needed.

SUMMARY

An aspect of the present invention relates to a nonnaturally occurring host having at least one hereditary alteration which increases the ability to transfer genetic molecules into the host as compared to an unaltered host.

In one nonlimiting embodiment, the nonnaturally occurring host cell is altered by deletion of an endogenous target locus.

In one nonlimiting embodiment, the naturally occurring host cell is altered to allow for genomic integration of an exogenous DNA sequence into the host cell.

Another aspect of the present invention relates to a method for identifying an endogenous target locus in a host cell which inhibits transformation efficiency. In this method, a single selected endogenous target locus in the host cell is modified. Transformation efficiency in this altered cell is then compared with transformation efficiency in the progenitor/wild-type host cell to determine if the alteration enhances transformation efficiency of the altered cell.

Another aspect of the present invention relates to a method for identifying an endogenous target locus in a host cell which inhibits electroporation efficiency. In this method, a single selected endogenous target locus in the host cell is modified. Electroporation of a plasmid in this altered cell is then compared with electroporation of the same plasmid in the progenitor/wild-type host cell to determine if the alteration enhances electroporation efficiency of the plasmid by the altered cell.

Another aspect of the present invention relates to a method for enhancing transformation efficiency of a host cell. In this method, an endogenous target locus in the host cell is identified which inhibits transformation efficiency. This endogenous target locus is then modified in the host cell.

Another aspect of the present invention relates to a method for modifying a host cell to allow for genomic integration of an exogenous DNA sequence via electroporation. In this method, an endogenous target locus in the host cell which inhibits electroporation efficiency is identified. The endogenous target locus is then modified in the host cell.

Another aspect of the present invention relates to a method for producing a biochemical from a nonnaturally occurring host of the present invention. In this method, a nonnaturally occurring host of the present invention is transformed with one or more exogenous nucleic acid sequences encoding one or more enzymes required for production of the biochemical. The biochemical is then produced in the nonnaturally occurring host cell.

Yet another aspect of the present invention relates to bio-derived, bio-based, or fermentation-derived products produced from the nonnaturally occurring hosts of the present invention.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DETAILED DESCRIPTION

Figure 1:
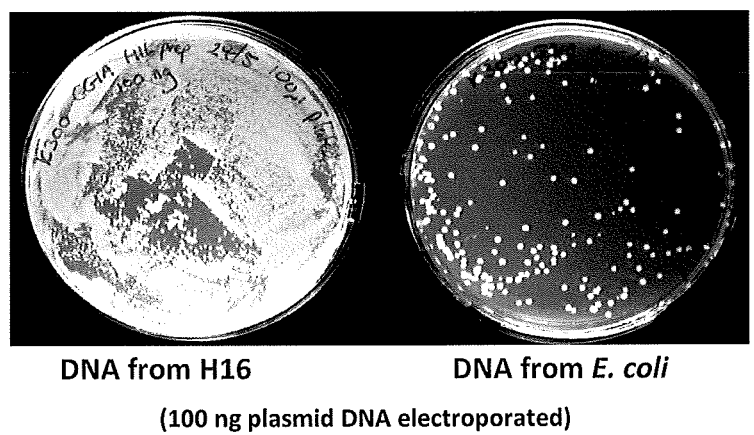
FIG. 1 provides a comparison demonstrating more efficient transformation of C. necator H16 with plasmid DNA purified from itself as compared to plasmid DNA purified from E. coli.

Disclosed herein are nonnaturally occurring hosts altered to increase their ability to transfer genetic molecules into the host cells and methods for their production.

The nonnaturally occurring hosts of the present invention are produced in accordance with the present invention by introducing at least one alteration into the host which increases the ability to transfer genetic molecules into the host as compared to an unaltered host.

In one nonlimiting embodiment, the alteration is a hereditary alteration. By "hereditary alteration" as used herein, it is meant a change, modification, variation or transformation in a genetic factor of a host including, but in no way limited to, an alteration in the genome of the host or an alteration in levels or types of protein expressed by the host. In one nonlimiting embodiment, the alteration increases the transformation efficiency of the altered nonnaturally occurring host as compared to an unaltered host. In one nonlimiting embodiment, transformation efficiency is increased for exogenous genetic molecules. In one nonlimiting embodiment, the alteration allows for genomic integration of an exogenous nucleic acid sequence via electroporation into the host. In one nonlimiting embodiment, the alteration increases the transformation efficiency of the altered non-naturally occurring host as compared to an unaltered host and allows for genomic integration of an exogenous DNA sequence via electroporation into the altered nonnaturally occurring host cell.

Various modifications and/or alterations to the host can be made. In one nonlimiting embodiment, the alteration is a hereditary alteration. In one nonlimiting embodiment, the alteration is a genetic alteration. In one nonlimiting embodiment, the alteration comprises deletion of an endogenous target locus. In one nonlimiting embodiment, the alteration comprises deletion of an endogenous target locus which interferes with transformation of an exogenous nucleic acid sequences. In one nonlimiting embodiment, the alteration is deletion of an endogenous endonuclease locus which cleaves any exogenous nucleic acid sequences. Endogenous genes of the nonnaturally occurring host may be further disrupted to prevent the formation of undesirable metabolites or prevent the loss of intermediates in the metabolic engineering pathway for which the cells will be used. Nonnaturally occurring hosts of the present invention may also be referred to as recombinant hosts, to as recombinant host cells, engineered cells, or engineered hosts.

By "genetic molecules" as used herein it is meant to include, but is not limited to, nucleic acid sequences such as DNA, RNA, cDNA, as well as expression vectors, plasmids and the like as well as amino acid sequences, polypeptides and proteins. In one nonlimiting embodiment, the genetic molecule may comprise an antibiotic resistance gene, a Kanamycin-based, Tetracycline-based, and/or Chloramphenicol-based plasmid, or any combination thereof.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

The methodologies disclosed herein were used to produce a nonnaturally occurring host cell with an approximate 10000-fold increase its ability to transfer genetic molecules as compared to the wild-type progenitor cells. In this non-limiting example, the altered host was C. necator H16. As shown in FIG. 1, C. necator H16 can be transformed more efficiently with plasmid DNA purified from itself rather than E. coli. While not being bound to any particular theory, it is believed that C. necator has specific DNA endonuclease(s) that cleave exogenous DNA. The DNA of C. necator is believed to be protected by methylation.

Accordingly, seven endonuclease loci were identified in the genome of C. necator H16. These target loci were then deleted individually and transformation efficiency was tested for each modified strain.

Results are shown in Table 1.

TABLE 1

| Target Locus | Colonies recovered following electroporation (75 ng plasmid DNA) |
|---|---|
| None (WT) | 92 |
| H16_A0006-9 | Lawn (4 repeats) |
| H16_A0014 | 127 |
| H16_A1147 | 28 |
| H16_A3579 | 128 |
| H16_B0176 | 40 |

TABLE 1-continued

| Target Locus | Colonies recovered following electroporation (75 ng plasmid DNA) |
|---|---|
| H16_PHG170 | 52 |
| H16_PHG327 | 101 |

As shown in Table 1, *C. necator* ΔH16_A0006-9 strain displayed a notable increase in transformation efficiency. In these experiments, *C. necator* ΔH16_A0006-9 was transformed with 75 ng plasmid DNA.

Ten-fold serial dilutions were then plated to enumerate the number of colonies with the plasmid. Results are shown in Table 2.

TABLE 2

| | ΔH16_A0006-9 strain | | | Wild-type control/Parental Strain |
|---|---|---|---|---|
| Dilution | Rep 1 | Rep 2 | Rep3 | Single replicate |
| 100 μl Neat | Lawn | Lawn | Lawn | 50 |
| $10^{-1}$ | Lawn | Lawn | Lawn | 2 |
| $10^{-2}$ | ~1000 | ~1000 | ~1000 | 1 |
| $10^{-3}$ | ~200 | ~1000 | ~800 | |
| $10^{-4}$ | 120 | ~800 | ~500 | |
| $10^{-5}$ | 90 | ~400 | 66 | |
| $10^{-6}$ | 55 | 200 | 25 | |
| $10^{-7}$ | | 110 | 63 | |

The transformation efficiency upon alteration in accordance with the methodologies of the present invention was increased by ~4 orders of magnitude. This is comparable to efficiencies routinely observed for laboratory *E. coli* strains (i.e., approx. $1 \times 10^{6-7}$ transformants per μg DNA).

Seven different plasmids were then electroporated into the *C. necator* ΔH16_A0006-9 strain. Plasmids included both replicons and suicide vectors involving 2 different antibiotic markers, Km and Tc, and various inserts. pBBR1MCS cloning vectors used have been described by Kovach et al. (Gene 1995 166:175-176). Results are depicted in Table 3.

Additional modifications which further improved transformation efficiency by approximately 3-fold included re-growth and recovery of cells in Super Optimal Broth, Catabolite Repression (SOC) broth, rather than Tryptone Soya Broth, DNA of 50-100 ng, and a two hour recovery following electroporation. With these improvements, transformation of wild-type H16 with 75 ng pBBR1-based kanamycin vector yielded 500-1000 colonies.

In general, transformation efficiency with pBBR1-based-tetracycline (Tc) plasmids (pBBR1-MCS3) was less as compared to the excellent transformation efficiency observed with pBBR1-based-kanamycin (Km) plasmids.

Figure 2:
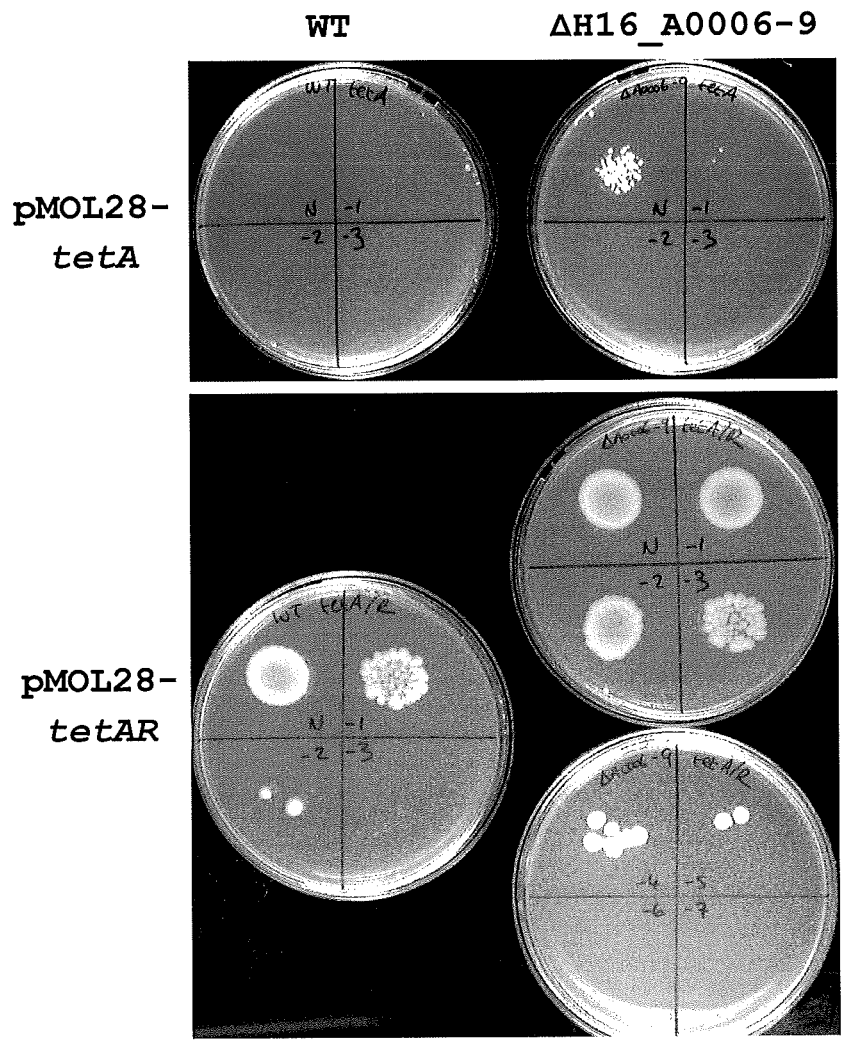
FIG. 2 compares transformation efficiency of C. necator H16 WT (left) and ΔH16_A0006-9 (right) transformed with 75 ng pMOL28-tetA (top panel) or pMOL28-tetAR (bottom panel). Each spot represents a 10-fold dilution. N=neat, $-1=10^{-1}$ etc.

When an independent pMOL28-based vector containing the tetAR cassette was constructed and used to transform *C. necator* wild-type (WT) and ΔH16_A0006-9, the presence of tetR increased transformation efficiency of £H16_A0006-9 by approximately 4 orders of magnitude and of WT by approximately 100-fold, relative to plasmid containing tetA only (Example 5 and FIG. 2). Functionally, tetR controls expression of tetA which is induced only in the presence of tetracycline (Bertram & Hillen, Microb Biotechnol. 2008 January; 1(1):2-16). The tetAR cassette characterized herein originates from RK2 plasmid and is described in detail by Waters et al. (Nucleic Acids Research 1983 11(17):6089-6105). The reason for increased TE of tetAR-based vectors remains unclear, although previous reports suggest that tetR expression prevents toxic build-up of the tetA membrane protein during recovery following transformation which may reduce the osmotic sensitivity of the cell, a phenomenon which has been suggested for *E. coli* (Stavropoulos & Strathdee, FEMS Microbiol Lett. 2000 Sep. 1; 190(1):147-50).

Further, high transformation efficiency was achieved with pBBR1-MCS2 variants carrying a range of different inserts (e.g. lycopene and IPA pathways), thus indicating that DNA sequence variations do not impact transformation efficiency/frequency.

Thus, as demonstrated by these experiments, the methodologies of the present invention were useful in substantially increasing the transformation efficiency of the altered host. Further, genomic integration of exogenous DNA sequences was achieved via electroporation rather than conjugation.

TABLE 3

| Cloning Plasmid | Purified from | Marker | Insert | Colony Count | Single colonies visible at dilution | Repeats |
|---|---|---|---|---|---|---|
| pBBR1-Km | *E. coli* | Kan | None | Lawn | $10^{-7}$ | >10 |
| pBBR1-MCS2-IPA | *E. coli* | Kan | IPA pathway | Lawn | $10^{-4}$ (7 colonies) | 2 |
| pBBR1-Km-lycopene pathway | *E. coli* | Kan | Lycopene pathway (*Erwinia herbicola*) | Lawn | $10^{-4}$ (62 colonies) | 1 |
| pBBR1-MCS3-mob- | *E. coli* | Tet | None | 50 | | 1 |
| PBBR1-MCS3 | *E. coli* | Tet | None | 0 | | 1 |
| pTc-INT-phaC::kan | *E. coli* | Kan | Kanamycin cassette from pBBR1-MCS2 | 5-25 | | 3 |
| pTc-INT-phaC::kan | *E. coli* | Tet | Kanamycin cassette from pBBR1-MCS2 | 0 | | 2 |

The significant advantages of the exemplified altered host cell demonstrated herein are indicative of host cells of the present invention being useful as metabolic engineering chassis.

By "metabolic engineering chassis" as used herein, it is meant an organism which readily accepts new genes and new biochemistry and serves as a frame in which to tailor a specific biochemical function while maintaining the growth behavior and application range of the respective wild type organism.

The significant advantages of the exemplified altered host cell presented herein are also demonstrative of the present invention providing a useful method for identifying an endogenous target locus in a host cell which inhibits transformation efficiency. In this method, single selected endogenous target loci in the host cell are modified. In one nonlimiting embodiment, the single selected endogenous target loci is deleted. In one nonlimiting embodiment, the endogenous target locus to be selected is an endonuclease locus. The transformation efficiency in these cells is then compared with the transformation efficiency in the progenitor/wild-type host cell. An increase in transformation efficiency in cells with a modified target locus is indicative of that target locus inhibiting transformation efficiently of the cell.

These advantages are also indicative of the present invention providing a useful method for identifying an endogenous target locus in a host cell which inhibits transformation efficiency via electroporation. In this method, single selected endogenous target loci in the host cell are modified. In one nonlimiting embodiment, the single selected endogenous target loci is deleted. In one nonlimiting embodiment, the endogenous target locus to be selected is an endonuclease locus. Electroporation of a plasmid in the altered cell is then compared with electroporation of the same plasmid in the progenitor/wild-type host cell. An increase in transformation efficiency of the plasmid in cells with a modified target locus is indicative of that target locus inhibiting transfer of plasmids in the progenitor/wild-type host cell.

In addition, these experiments demonstrate the usefulness of these methodologies in enhancing transformation efficiency of a host cell. In these methods, an endogenous target locus in a host cell which inhibits transformation efficiency can be identified as described and exemplified herein. In one nonlimiting embodiment, the endogenous target locus is an endonuclease locus. Once identified, the endogenous target locus can be modified to produce a nonnaturally occurring host cell having at least one alteration with increased ability to transfer genetic molecules into the host cell as compared to an unaltered host cell. In one nonlimiting embodiment, the endogenous target locus is deleted.

The experiments also demonstrate the usefulness of these methodologies in modifying a host cell to allow for genomic integration of an exogenous DNA sequence via electroporation. In these methods, an endogenous target locus in the host cell which inhibits transformation efficiency is identified as described and exemplified herein. In one nonlimiting embodiment, the endogenous target locus is an endonuclease locus. Once identified, the endogenous target locus can be modified to produce a nonnaturally occurring host cell allowing for genomic integration of an exogenous DNA sequence via electroporation. In one nonlimiting embodiment, the endogenous target locus is deleted.

The nonnaturally occurring host cells of the present invention are useful in methods for producing biochemicals. In these methods, a nonnaturally occurring host cell of the present invention is transformed with one or more exogenous nucleic acid sequences encoding one or more enzymes required for production of the biochemical. The cells are then subjected to selected conditions in which the biochemical is produced. For example, a fermentation strategy can be used that entails anaerobic, micro-aerobic or aerobic cultivation. A fermentation strategy can entail nutrient limitation such as nitrogen, phosphate or oxygen limitation. A cell retention strategy using a ceramic hollow fiber membrane can be employed to achieve and maintain a high cell density during fermentation. The principal carbon source fed to the fermentation can derive from a biological or non-biological feedstock. The biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles or municipal waste. The non-biological feedstock can be, or can derive from, natural gas, syngas, $CO_2/H_2$, methanol, ethanol, non-volatile residue (NVR) a caustic wash waste stream from cyclohexane oxidation processes or waste stream from a chemical or petrochemical industry.

In one nonlimiting embodiment, at least one of the enzymatic conversions may comprise gas fermentation within the host cell. In this embodiment, the gas fermentation may comprise at least one of natural gas, syngas, $CO_2/H_2$, methanol, ethanol, non-volatile residue, caustic wash from cyclohexane oxidation processes, or waste stream from a chemical or petrochemical industry. In one nonlimiting embodiment, the gas fermentation comprises $CO_2/H_2$.

In addition, the present invention provides bio-derived, bio-based, or fermentation-derived products produced using the methods and/or cells disclosed herein. Examples of such products include, but are not limited to, compositions comprising at least one bio-derived, bio-based, or fermentation-derived compound or any combination thereof, as well as polymers, molded substances, formulations and semi-solid or non-semi-solid streams comprising one or more of the bio-derived, bio-based, or fermentation-derived compounds or compositions, combinations or products thereof.

The following section provides further illustration of the cells and methods of the present invention. These working examples are illustrative only and are not intended to limit the scope of the invention in any way.

EXAMPLES

Example 1: Identification of Endonuclease Loci in Genome of *C. necator* H16

The *C. necator* H16 genome was queried for annotated open reading frames (ORFS) containing the annotation 'nuclease' using genome analysis software (GeneData). The list was rationalized based on protein homology to known restriction endonuclease genes to a final list of seven targets.

Example 2: Deletion of Individual Target Loci

Standard allele exchange protocols were carried out. 400 to 800 base pairs upstream (LHA) and downstream (RHA) of each individual endonuclease locus of *C. necator* H16 along with the first five and final five codons of each gene were amplified by PCR using NEB Q5 DNA polymerase. Appropriate homologous overhangs were designed onto each primer to facilitate cloning by Gibson Assembly (see Gibson et al. Nat Methods. 2009 6(5):343-5). Purified PCR-amplified fragments were cloned into a PvuI-digested p(Tc-INT-phaC::kan) plasmid.

Example 3: Transfer of Allele Exchange Constructs

Verified allele exchange constructs were transferred to the conjugative bacterial donor *E. coli* S17-1 by transformation and then to *C. necator* H16 by conjugation. *C. necator* trans-conjugants were selected on media supplemented with appropriate antibiotics. Plates were incubated until individual colonies were visible. Three independent clones were cultured in liquid medium with no antibiotic and then plated on appropriate media supplemented with sucrose to select for double crossover integrants. Individual colonies were screened for chromosomal deletion by colony PCR.

Example 4: Electroporation/Transformation Efficiency

Electroporation/transformation efficiency was tested for each modified strain as follows. Restriction endonuclease mutants were transformed with pBBR1-based plasmid by electroporation. The cell/plasmid mixture was recovered and then plated onto medium with appropriate antibiotic. The plates were incubated until individual colonies were visible. Colonies were counted and the transformation efficiency calculated.

Example 5: Improving Transformation Efficiency of Tetracycline (Tc)-Based Plasmids in *C. necator* ΔH16_A0006-9

An independent pMOL28-based vector containing the tetAR cassette (as depicted in SEQ ID NO:1 with TetA at nucleotides 1-1200, the regulatory region at nucleotides 1248-1305 and TetR at nucleotides 1306-1956) was constructed by Gibson Assembly and used to transform *C. necator* wild-type (WT) and ΔH16_A0006-9. The presence of tetR increased transformation efficiency of ΔH16A0006-9 by approximately 4 orders of magnitude and of WT by approximately 100-fold, relative to plasmid containing tetA only (FIG. 2).

What is claimed is:

1. A nonnaturally occurring organism having at least one hereditary alteration which increases the ability to transfer genetic molecules into the organism as compared to an unaltered organism, wherein the nonnaturally occurring organism is a strain of *Cupriavidus necator* and wherein the alteration is deletion of an endogenous target locus H16_A0006-9.

2. The nonnaturally occurring organism of claim 1 wherein the alteration increases transformation efficiency.

3. The nonnaturally occurring organism of claim 1 wherein the alteration allows for genomic integration of an exogenous DNA sequence via electroporation into the organism.

4. The nonnaturally occurring organism of claim 1 wherein the alteration increases transformation efficiency and allows for genomic integration of an exogenous DNA sequence via electroporation into the organism.

5. The nonnaturally occurring organism of claim 1 wherein the genetic molecule comprises an antibiotic resistance gene, a Km-based, Tc-based, and/or Cm-based plasmid, or any combination thereof.

* * * * *